United States Patent [19]

Zaiger

[11] Patent Number: Plant 5,276

[45] Date of Patent: Aug. 28, 1984

[54] PEACH TREE (HONEY BEE)

[76] Inventor: Chris F. Zaiger, 537 Rosemore Ave., Modesto, Calif. 95351

[21] Appl. No.: 453,770

[22] Filed: Dec. 27, 1982

[51] Int. Cl.[3] ..... A01H 5/03

[52] U.S. Cl. ..... Plt./43

[58] Field of Search ..... Plt./43

*Primary Examiner*—Robert E. Bagwill

[57] ABSTRACT

The new variety of peach tree characterized by its dwarf size (6 to 7 ft.), non-vigorous, dense and spreading in growth, the tree having dense foliage, large showy pink flowers and a regular and productive bearer of large size, early ripening, firm, yellow flesh, freestone fruit with excellent eating quality.

1 Drawing Figure

ORIGIN OF THE VARIETY

The present variety of peach tree was originated by me in my experimental orchard, located near Modesto, Calif., as a selected seedling from a large number of second generation seedlings, from a cross between Spring Crest Peach (unpatented) and a genetic dwarf peach seedling of unknown parentage. The selection was maintained under careful and continual observation, during which time it was selected for reproduction due to its distinct and desireable characteristics.

ASEXUAL REPRODUCTION OF THE VARIETY

The present variety of peach tree was asexually propagated by budding as performed by me in my experimental orchard at Modesto, Calif., shows that said characteristic come true to form and are established and transmitted through succeeding propagations.

SUMMARY OF THE VARIETY

The herein variety relates to a new and distinct variety of peach tree which is dwarf in size (6 to 7 ft.), dense and spreading in growth; the tree being a regular and productive bearer of large size, firm, freestone fruit ripening in the early season. The fruit further being characterized by its juicy, melting texture with excellent eating quality.

PHOTOGRAPH OF THE VARIETY

The accompanying photographs show reproductions in color of the foliage and fruit of my new variety, with the upper and lower surface of the leaves being illustrated, also an exterior and a sectional view of the fruit being shown with the stone remaining in place. These illustrations were taken shortly after being picked at maturity, (eating ripe). The colors are as nearly true as is reasonably possible in a color representation of this type.

DESCRIPTION OF THE VARIETY

The following is a detailed botanical description of the fruit and foliage of my new dwarf peach variety, as based upon observations of specimens grown at Modesto, Calif., with color terminology (except in common terms) in accordance with Reinhold color Atlas by A. Korneruf and J. H. Wanscher.

Tree:

*Size.*—Dwarf (6 to 8 ft.)

*Vigor.*—Non-vigorous.

*Form.*—Spreading.

*Density.*—Dense.

*Bearing.*—Regular.

*Production.*—Productive.

Trunk:

*Form.*—Stocky.

*Texture.*—Shaggy.

Branches:

*Size.*—Stocky.

*Texture.*—Medium rough.

Leaves:

*Size.*—Large. Average length—6½". Average width—1".

Margin.—Crenate.

Thickness.—Medium.

Petiole.—Medium length. Medium thickness.

*Glands.*—Average number 2. Range 2 to 4 usually positioned on base of leaf blade or on petiole near leaf blade.

*Color.*—Upper surface—dark green (29-E-5) to (29-E-7). Lower surface—grayish green (30-E-6) to (30-E-8).

Flower buds:

*Size.*—Large.

*Length.*—Medium.

Flowers:

*Size.*—Large, showy.

*Color.*—Pink.

*Pollen.*—Present.

*Blooming Period.*—Feb. 23, 1981 to Mar. 8, 1981.

Fruit:

*Maturity.*—Date of first picking—June 15, 1981. Date of last picking—June 22, 1981.

*Size.*—Large. Average diameter axially—2⅞". Average transversely in suture plane—3".

*Form.*—Semi-uniform—slightly larger on one side. Nearly globose.

*Suture.*—Shallow extends from base to apex.

*Cavity.*—Slightly elongated in suture plane. Average depth—5/16". Average breadth—½".

*Apex.*—Short—slightly rounded to distinct point.

Skin:

*Thickness.*—Medium.

*Texture.*—Medium.

*Tendency to crack.*—None.

*Down.*—Moderate. Medium length.

*Color.*—Bright yellow undercolor (4-A-8) to (4-B-8). Red blush covering most of the surface of the peach (8-A-8) to (8-B-8).

Flesh:

*Texture.*—Moderately firm, melting when eating ripe.

*Juice.*—Moderate to abundant.

*Flavor.*—Subacid.

*Ripens.*—Evenly.

Stone:

*Type.*—Freestone.

*Size.*—Average length—1⅛". Average breadth—1". Average thickness—¾".

*Form.*—Ovid.

*Base.*—Mostly straight.

*Sides.*—Mostly equal—slightly larger with extention of wings.

*Surface.*—Pitted throughout.

*Color.*—Light brown (8-C-6).

*Tendency to split.*—Very slight.

Use: Home and local market.

Keeping quality: Medium.

The dwarf peach tree and its fruit herein described may vary in slight detail due to soil and climatic conditions under which the variety may be grown; the present description being of the variety as grown in Modesto, Calif.

The following is claimed:

1. A new and distinct variety of peach tree as illustrated and described by its dwarf size (6 to 7 ft.), having spreading and dense growth with close leaf nodes, attractive foliage, large showy flowers and a productive and regular bearer of early maturing, large, yellow flesh, freestone fruit of excellent eating quality.

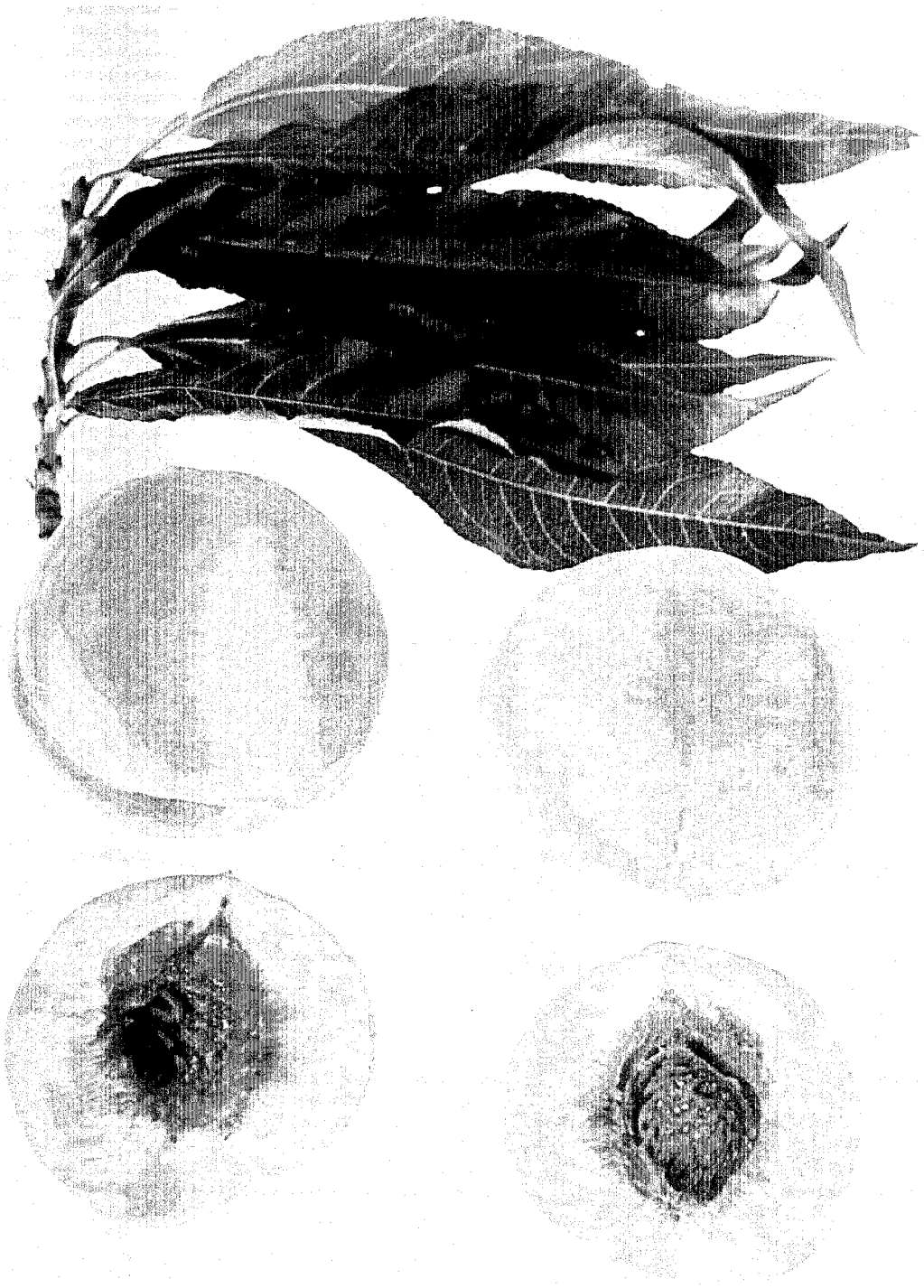

* * * * *